United States Patent
Yoo et al.

(10) Patent No.: US 12,306,162 B2
(45) Date of Patent: May 20, 2025

(54) HYDROGEN SENSOR AND METHOD FOR MANUFACTURING THE SAME

(71) Applicants: HYUNDAI MOTOR COMPANY, Seoul (KR); KIA CORPORATION, Seoul (KR)

(72) Inventors: Il Seon Yoo, Suwon-si (KR); Hyun Soo Kim, Yongin-si (KR); Jang Hyeon Lee, Gunpo-si (KR); Dong Gu Kim, Suwon-si (KR); Dae Sung Kwon, Seoul (KR)

(73) Assignees: HYUNDAI MOTOR COMPANY, Seoul (KR); KIA CORPORATION, Seoul (KR)

( * ) Notice: Subject to any disclaimer, the term of this patent is extended or adjusted under 35 U.S.C. 154(b) by 486 days.

(21) Appl. No.: 17/962,689

(22) Filed: Oct. 10, 2022

(65) Prior Publication Data
US 2023/0194494 A1    Jun. 22, 2023

(30) Foreign Application Priority Data

Dec. 20, 2021    (KR) .......................... 10-2021-0182300

(51) Int. Cl.
*G01N 33/00*    (2006.01)
*G01N 27/16*    (2006.01)

(52) U.S. Cl.
CPC ........... *G01N 33/005* (2013.01); *G01N 27/16* (2013.01)

(58) Field of Classification Search
CPC .............................. G01N 27/16; G01N 33/005
USPC ....................................................... 73/31.05
See application file for complete search history.

(56) References Cited

U.S. PATENT DOCUMENTS

| 10,017,379 B2 | 7/2018 | Rajaraman et al. |
| 2014/0208838 A1* | 7/2014 | Moon ............ G01N 27/16 73/114.75 |
| 2014/0290338 A1* | 10/2014 | Kim ............. G01N 27/414 73/31.06 |

FOREIGN PATENT DOCUMENTS

| JP | 3585082 B2 | 11/2004 |
| JP | 2007-278996 A | 10/2007 |
| JP | 2008-275588 A | 11/2008 |
| JP | 4576582 B2 | 11/2010 |
| KR | 10-0225069 B1 | 10/1999 |
| KR | 10-0905106 B1 | 6/2009 |
| KR | 2010-0026810 A | 3/2010 |
| WO | WO-2010084916 A1 * | 7/2010 ............ G01N 27/16 |

OTHER PUBLICATIONS

Translation of WO-2010084916-A1 (Year: 2010).*

* cited by examiner

*Primary Examiner* — Nathaniel T Woodward
(74) *Attorney, Agent, or Firm* — MCDONNELL BOEHNEN HULBERT & BERGHOFF LLP

(57) ABSTRACT

A hydrogen sensor includes a substrate, an insulating part formed on the substrate and provided with a plurality of holes, a first catalyst part formed on an upper end of the insulating part to accelerate the reaction between hydrogen and oxygen, a second catalyst part formed on a surface of the holes to accelerate the reaction between hydrogen and oxygen, and a heater part disposed inside the insulating part to heat the first catalyst part and the second catalyst part, and having an temperature increased by reaction heat generated by the reaction between hydrogen and oxygen.

10 Claims, 6 Drawing Sheets

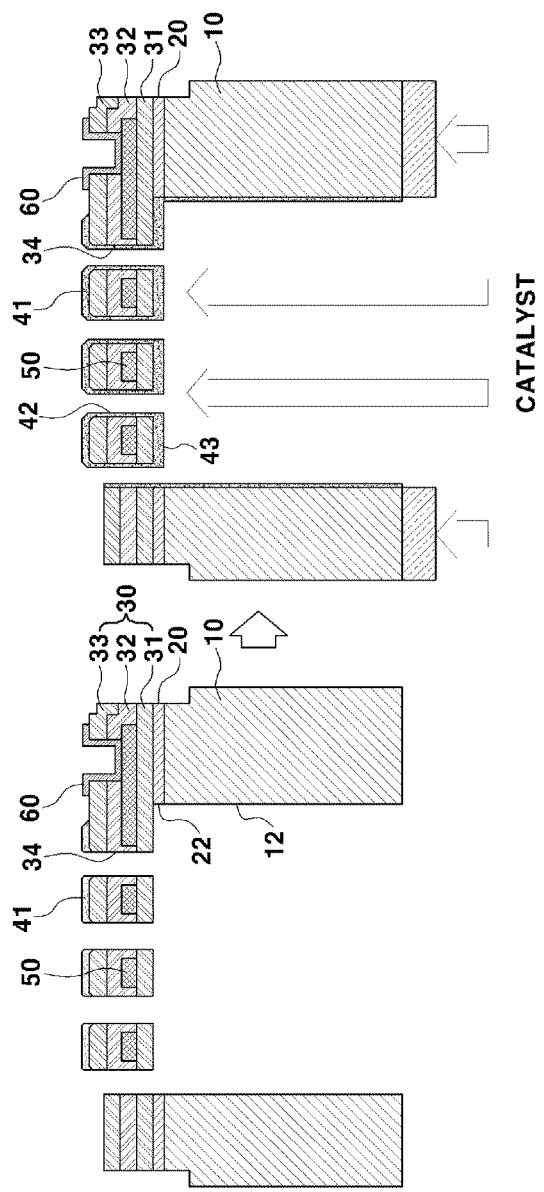

HYDROGEN SENSOR AND METHOD FOR MANUFACTURING THE SAME

CROSS REFERENCE TO RELATED APPLICATIONS

This application claims under 35 U.S.C. § 119(a) the benefit of priority to Korean Patent Application No. 10-2021-0182300 filed on Dec. 20, 2021, the entire contents of which are incorporated herein by reference.

BACKGROUND

(a) Technical Field

The present disclosure relates to a hydrogen sensor and a method for manufacturing the same for improving hydrogen sensing performance.

(b) Background Art

Currently, interest in hydrogen as an eco-friendly alternative energy is continuously increasing. Therefore, research is being conducted in various fields such as automobiles, fuel cells, and internal combustion engines, which are rapidly replacing existing fossil fuels, and related industrial fields being researched and developed are also increasing.

However, since hydrogen has a high risk of leakage and explosion due to its high diffusivity, safety measures related to safety against hydrogen leakage are desired. Therefore, safety measures are being prepared using various hydrogen sensors around hydrogen storages and hydrogen-related devices, and research and development related to the hydrogen sensor are being actively conducted.

In general, the hydrogen sensor is divided into a semiconductor type, a catalytic combustion type, a field effect transistor (FET) type, an electrolyte type (electrochemical type), an optical fiber type, and a thermoelectric type according to a detection method.

Among them, the catalytic combustion type hydrogen sensor converts the reaction heat generated when hydrogen and oxygen react into an electric signal to measure the degree of the reaction, and uses a catalyst that promotes complete oxidation to increase a reaction rate.

In addition, in the catalytic combustion type hydrogen sensor, a catalyst part is formed on a heater to activate the catalyst, and when a combustion reaction occurs, a temperature rises and therefore, a resistance value of the heater varies.

Currently, the catalytic combustion type hydrogen sensor is manufactured in a bead type or manufactured using a micro electro mechanical system (MEMS) manufacturing technology using a thin film material.

A conventional catalytic combustion type hydrogen sensor manufactured using the MEMS manufacturing technology is provided with a catalyst part formed on a substrate and a heater for activating the catalyst part.

The catalytic combustible type hydrogen sensor can adopt a structure of increasing a surface area of the catalyst part to improve the catalyst reaction, but since the catalyst part is formed of a single layer on an uppermost end of the substrate, there is a structural limitation in increasing the surface area of the catalyst part.

The above information disclosed in this Background section is only for enhancement of understanding of the background of the disclosure and accordingly it may include information that does not form the prior art that is already known in this country to a person of ordinary skill in the art.

SUMMARY

The present disclosure has been made in efforts to solve the above problem associated with the related art, and an object of the present disclosure is to provide a hydrogen sensor configured to increase a surface area of a catalyst part that promotes reaction between hydrogen and oxygen, thereby improving hydrogen sensing performance, and a method for manufacturing the same.

The object of the present disclosure is not limited to the aforementioned object, and other objects of the present disclosure not mentioned will be clearly understood to those skilled in the art to which the present disclosure pertains from the following description.

To achieve the object, the present disclosure provides a hydrogen sensor including a substrate, an insulating part formed on the substrate and comprising a plurality of holes, a first catalyst part formed on an upper end of the insulating part to accelerate the reaction between hydrogen and oxygen, a second catalyst part formed on a surface each of the plurality of holes to accelerate the reaction between hydrogen and oxygen, and a heater part disposed inside the insulating part to heat the first catalyst part and the second catalyst part, and having a temperature increased by reaction heat generated by the reaction between hydrogen and oxygen.

According to the exemplary embodiment of the present disclosure, a thin film part protecting the insulating part is formed on the upper end of the substrate, and the thin film part is positioned under the insulation part.

In addition, according to the exemplary embodiment of the present disclosure, a third catalyst part is formed on the lower end of the insulating part, the substrate and the thin film part have a through part formed in central portions thereof, and the third catalyst part is positioned above the through part.

In addition, according to the exemplary embodiment of the present disclosure, the hole is formed to extend from the upper end to the lower end of the insulating part to communicate with the through part.

In addition, according to the exemplary embodiment of the present disclosure, the second catalyst part is formed in a thickness smaller than a radius of the hole.

In addition, according to the exemplary embodiment of the present disclosure, the insulating part is composed of a first insulating film stacked on an upper end of the thin film part, and having the third catalyst part disposed on a lower end thereof; a second insulating film formed on an upper end of the first insulating film to cover the heater part; and a third insulating film formed on an upper end of the second insulating film.

In addition, according to the exemplary embodiment of the present disclosure, a connection pad penetrating the second insulating film and the third insulating film to be in contact with a surface of the heater part is provided.

Meanwhile, the present disclosure also provides a method for manufacturing a hydrogen sensor including manufacturing and preparing a substrate, and forming a thin film part on the substrate, forming a lower catalyst part by depositing a catalyst accelerating the reaction between hydrogen and oxygen on the thin film part, forming a first insulating film on the thin film part to cover the lower catalyst part, forming a heater part on an upper end of the first insulating film in a predetermined pattern, forming a second insulating film on the first insulating film to cover the heater part, forming a third insulating film on an upper end of the second insulating film, forming a plurality of holes penetrating the insulating films and the lower catalyst part, forming a first catalyst part and a second catalyst part by depositing a catalyst on an upper end of the third insulating film and a surface of the hole, and forming a through part in central portions of the substrate and the thin film part by etching the substrate and the thin film part.

According to the exemplary embodiment of the present disclosure, the method includes forming a pad hole by etching the second insulating film and the third insulating film and then, forming a connection pad in contact with the surface of the heater part in the pad hole.

In addition, according to the exemplary embodiment of the present disclosure, the forming of the connection pad is performed between the forming of the third insulating film and the forming of the first catalyst part and the second catalyst part.

According to the above configuration, the hydrogen sensor according to the present disclosure is configured to increase the surface area of the catalyst part that promotes the reaction between hydrogen and oxygen, thereby improving the hydrogen sensing performance.

The effect of the present disclosure is not limited to the aforementioned effect, and other effects of the present disclosure not mentioned will be clearly understood to those skilled in the art to which the present disclosure pertains from the following description.

It is understood that the term "automotive" or "vehicular" or other similar term as used herein is inclusive of motor automotives in general such as passenger automobiles including sports utility automotives (operation SUV), buses, trucks, various commercial automotives, watercraft including a variety of boats and ships, aircraft, and the like, and includes hybrid automotives, electric automotives, plug-in hybrid electric automotives, hydrogen-powered automotives and other alternative fuel automotives (e.g., fuels derived from resources other than petroleum). As referred to herein, a hybrid automotive is an automotive that has two or more sources of power, for example both gasoline-powered and electric-powered automotives.

BRIEF DESCRIPTION OF THE FIGURES

The above and other features of the present disclosure will now be described in detail with reference to certain exemplary examples thereof illustrated in the accompanying drawings which are given herein below by way of illustration only, and thus are not limitative of the present disclosure, and wherein:

FIG. 6 is a diagram showing the manufacturing process of the hydrogen sensor according to another exemplary embodiment of the present disclosure.

Figure 1:
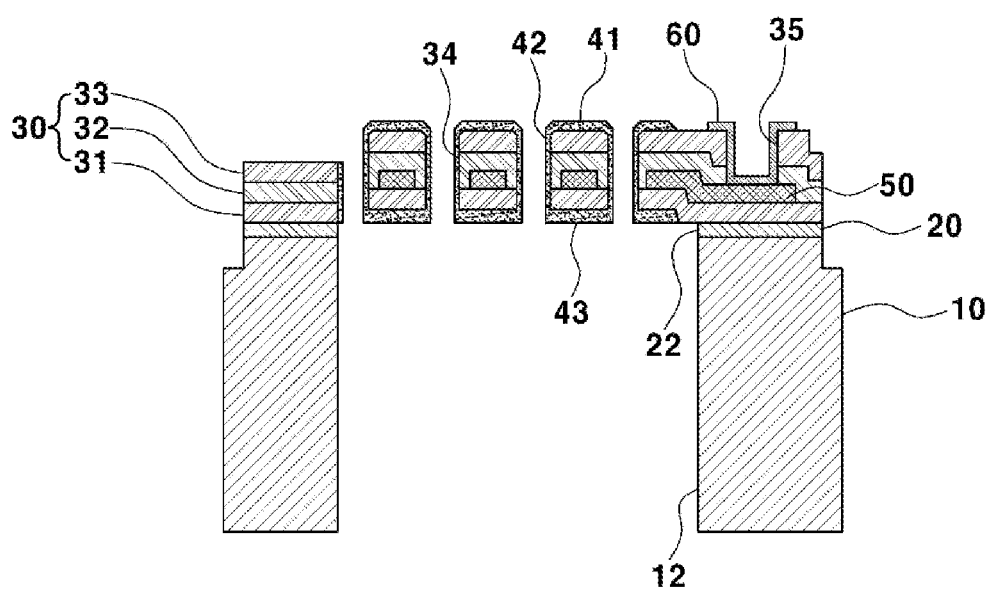
FIG. 1 is a diagram schematically showing a cross-sectional structure of a hydrogen sensor according to an exemplary embodiment of the present disclosure.

It should be understood that the appended drawings are not necessarily to scale, presenting a somewhat simplified representation of various preferred features illustrative of the basic principles of the disclosure. The specific design features of the present disclosure as disclosed herein, including, for example, specific dimensions, orientations, locations, and shapes will be determined in section by the particular intended application and use environment.

In the figures, reference numbers refer to the same or equivalent sections of the present disclosure throughout the several figures of the drawing.

DETAILED DESCRIPTION

Specific structural or functional descriptions presented in exemplary embodiments of the present disclosure are only exemplified for the purpose of describing the exemplary embodiments according to the concept of the present disclosure, and the exemplary embodiments according to the concept of the present disclosure can be carried out in various forms.

In addition, throughout the present specification, when a certain part "comprises" a certain component, it means that other components can be further included, rather than excluding other components, unless specially stated otherwise.

In addition, in the present specification, when a certain component is said to be "on" or "above" another component, this can include not only a case where the certain component is "directly above" another component but also a case where there are other components therebetween. In addition, when a certain component is said to be "below" or "under" another component, this can include not only a case where the certain component is "directly below" another component but also a case where there are other components therebetween.

Meanwhile, in the present disclosure, terms such as first and/or second can be used to describe various components, but the components are not necessarily limited to the terms. The terms are used only for the purpose of distinguishing one component from other components. For example, a first component can be referred to as a second component, and similarly, the second component can also be referred to as the first component without departing from the scope according to the concept of the present disclosure.

A general catalytic combustion type hydrogen sensor will be briefly described before describing a hydrogen sensor according to the present disclosure.

In general, a catalytic combustion type hydrogen sensor is configured to measure the concentration of hydrogen in a detection space (e.g., atmosphere) by converting reaction heat generated when hydrogen and oxygen react into an electric signal, and uses a catalyst to increase a reaction rate between hydrogen and oxygen.

In other words, the catalytic combustion type hydrogen sensor is configured to detect the concentration of hydrogen in the detection space based on the reaction heat generated from the oxidation reaction of a hydrogen gas using the catalyst.

The catalytic combustion type hydrogen sensor is configured to include a sensing element including a catalyst part, a compensating element not including the catalyst part, and an electric circuit part electrically connected to the sensing element and the compensating element. The sensing element has a structure in which the catalyst part is added to the compensating element. The electric circuit part is configured to detect a hydrogen concentration based on a difference value between the reaction heat sensed by the sensing element and the reaction heat sensed by the compensating element.

The catalytic combustion type hydrogen sensor can have a structure in which the sensing element, the compensating element, and the electric circuit part are provided in one package.

The present disclosure is to improve the sensing element of the aforementioned catalytic combustion type hydrogen sensor, and is mainly characterized by a structure of the sensing element, and the compensating element and the electric circuit part can be applied in the same manner as in the related art.

In other words, the present disclosure relates to a catalytic combustion type hydrogen sensor including the sensing element, the compensating element, and the electric circuit part, but since the compensating element and the electric circuit part are known technologies, here, a detailed description of the compensating element and the electric circuit part will be omitted.

The catalytic combustion type hydrogen sensor according to the present disclosure is configured to increase a surface area of a catalyst part that promotes complete oxidation of hydrogen, thereby improving hydrogen sensing performance.

Hereinafter, an exemplary embodiment of the present disclosure will be described with reference to the accompanying drawings. Matters expressed in the accompanying drawings can be different from the forms actually implemented in the drawings shown for easily describing the exemplary embodiment of the present disclosure.

Figure 2A:
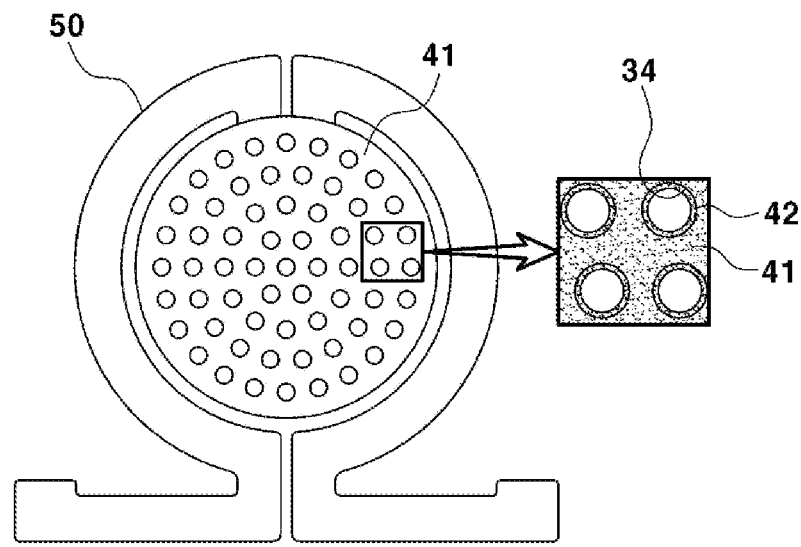
FIGS. 2A and 2B are diagrams viewed from above and below the main part of the hydrogen sensor according to the exemplary embodiment of the present disclosure.
Figure 2B:
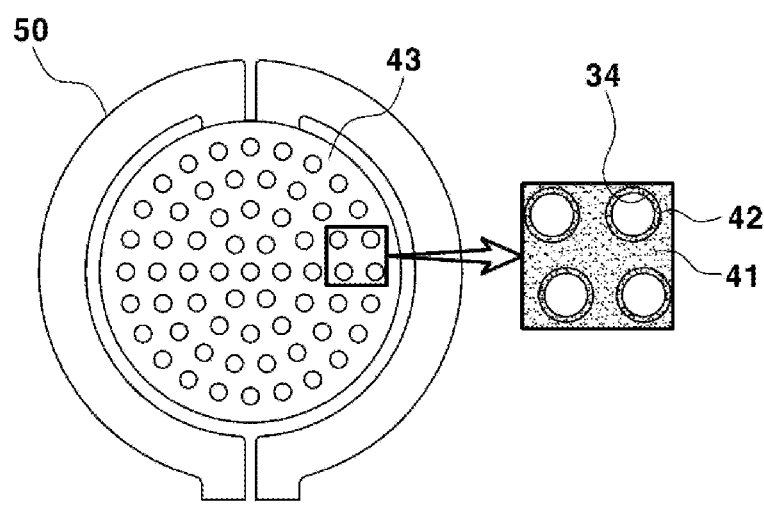

FIG. 1 is a diagram schematically showing a cross-sectional structure of a hydrogen sensor according to an exemplary embodiment of the present disclosure, and FIGS. 2A and 2B are diagrams viewed from above and below the main part of the hydrogen sensor according to the exemplary embodiment of the present disclosure.

As shown in FIG. 1, a hydrogen sensor according to an exemplary embodiment of the present disclosure is configured to include a substrate 10, a thin film part 20, an insulating part 30, a first catalyst part 41, a second catalyst part 42, a third catalyst part 43, and a heater part 50.

The substrate 10 is formed in a plate shape having a predetermined thickness, and has a through part 12 provided in a central portion thereof. The through part 12 extends in a thickness direction of the substrate 10. The through part 12 can extend from an upper end to a lower end of the substrate 10. The substrate 10 can be made of a silicon (Si) material.

The thin film part 20 is formed to be stacked on a surface of the substrate 10 in a thin film form and disposed below the insulating part 30. The thin film part 20 serves to protect the insulating part 30 and the third catalyst part 43 on the upper end of the substrate 10.

If the substrate 10 is etched from the lower end thereof, the third catalyst part 43, the insulating part 30, etc. disposed above the substrate 10 can be damaged. The thin film part 20 protects the third catalyst part 43 and the insulating part 30 formed on the upper end thereof, thereby preventing the third catalyst part 43 and the insulating part 30 from being damaged. The thin film part 20 can be made of, for example, silicon oxide.

Like the substrate 10, the thin film part 20 also has a through part 22 formed in a central portion thereof. The through part 22 extends in the thickness direction of the thin film part 20, and is formed in the same radius as that of the through part 12 of the substrate 10 and disposed on the same line.

The insulating part 30 is formed to be stacked on the substrate 10 in a multilayer thin film structure, and is configured in a porous structure provided with a plurality of holes 34.

The insulating part 30 is configured in a structure of surrounding the heater part 50 and serves to electrically insulate and protect the heater part 50 of a predetermined pattern. In addition, the insulating part 30 prevents contact and reaction between the heater part 50 and the catalyst parts 41, 42, 43 and separates and protects the heater part 50 from the catalyst parts 41, 42, 43.

To this end, the insulating part 30 is configured in a multilayer thin film structure including a first insulating film 31, a second insulating film 32, and a third insulating film 33.

The heater unit 50 is formed to be stacked on an upper end of the first insulating film 31 in a predetermined pattern, and is covered with the second insulating film 32 and the third insulating film 33 and disposed in the insulating part 30. In other words, the heater part 50 is completely surrounded by the insulating part 30 and disposed in the insulating part 30. In other words, the heater part 50 is disposed in the insulating part 30 in a sandwiched form. The heater part 50 is activated by heating the first catalyst part 41, the second catalyst part 42, and the third catalyst part 43.

The first insulating film 31 is formed to be stacked on the upper end of the thin film part 20 in the form of a thin film. The first insulating film 31 can be made of silicon nitride, which is an insulating material. For example, the first insulating film 31 can be made of $Si_3N_4$.

The second insulating film 32 is formed to be stacked on the upper end of the first insulating film 31 to cover the heater part 50 formed on the upper end of the first insulating film 31. The second insulating film 32 directly covers the surface of the heater part 50 to be in direct contact with the heater part 50. The second insulating film 32 can be made of silicon oxide, and formed in the form of the thin film. For example, the second insulating film 32 can be made of tetraethyl orthosilicate (TEOS).

The third insulating film 33 is formed to be stacked on an upper end of the second insulating layer 32 in the form of a thin film. The third insulating film 33 can be made of silicon nitride, and for example, made of $Si_3N_4$ like the first insulating layer 31.

As described above, the insulating part 30 configured in the multilayer thin film structure is provided with the plurality of holes 34. Each hole 34 is formed to extend in the thickness direction of the insulating part 30. In other words, the hole 34 is formed to extend in the stacking direction of the insulating films 31, 32, and 33.

The hole 34 extends to penetrate from the upper end to the lower end of the insulating part 30. In other words, the hole 34 extends from the lower end of the first insulating film 31 to the upper end of the third insulating film 33. The first insulating film 31 is the lowermost layer of the insulating part 30, and the third insulating film 33 is the uppermost layer of the insulating part 30.

In addition, each hole 34 is disposed above the through parts 12, 22 and directly communicates with the through parts 12, 22. Each hole 34 serves as a gas passage between the second catalyst part 42 and the third catalyst part 43. In other words, the second catalyst part 42 and the third catalyst part 43 can be in direct contact with hydrogen and air through the hole 34.

Each hole 34 can be distributed and disposed in a defined region of the insulating part 30. For example, the hole 34 can be evenly distributed in a predetermined region of the insulating part 30 located above the through parts 12, 22.

The catalyst parts 41, 42, and 43 formed to be stacked on the surface of the insulating part 30 serve to promote the oxidation reaction and complete oxidation of a hydrogen gas. The catalyst parts 41, 42, and 43 can be made of a material such as platinum (Pt) or palladium (Pd).

The first catalyst part 41 is formed to be stacked on the upper end of the insulating part 30 in the form of a thin film. In other words, the first catalyst part 41 is disposed to be stacked on the upper end of the third insulating film 33.

The second catalyst part 42 is formed to be stacked on the surface of the hole 34 in the form of a thin film, and the third catalyst part 43 is formed to be stacked on the lower end of the insulating part 30 in the form of a thin film. In other words, the third catalyst part 43 is disposed to be stacked on the lower end of the first insulating film 31.

Referring to FIG. 2A, the second catalyst part 42 is formed in a thickness smaller than the radius of the hole 34. Specifically, the second catalyst part 42 is formed on the surface of the hole 34 at a thickness smaller than the radius of the hole 34 by a predetermined value or more. Therefore, the hole 34 is not blocked by the second catalyst part 42 and can normally serve as the gas passage.

The third catalyst part 43 is disposed above the through parts 12, 22 of the substrate 10 and the thin film part 20. Therefore, the third catalyst part 43 can be in contact with hydrogen and air through the through parts 12, 22 together with the hole 34.

Meanwhile, FIGS. 2A and 2B schematically show a predetermined section of the insulating part surrounded by the catalyst part, and the heater part having a central portion sandwiched in the insulating part. FIG. 2A is a diagram viewed from above a predetermined section of the insulating part, and FIG. 2B is a diagram viewed from below a predetermined section of the insulating part.

As shown in FIGS. 2A and 2B, both ends of the heater part 50 can extend to the outside of the predetermined section of the insulating part 30 (i.e., a portion surrounded by the catalyst parts 41, 42, 43). At this time, both ends of the heater part 50 can extend in a semicircular shape surrounding the predetermined section of the insulating part 30.

Although not shown in FIGS. 2A and 2B, the central portion of the heater part 50 is sandwiched and disposed in the insulating part 30 in a state of being surrounded by the catalyst parts 41, 42, 43. In addition, although FIGS. 2A and 2B show only both ends of the heater part 50, both ends of the heater part 50 are also sandwiched and disposed in the insulating part 30. In other words, both ends of the heater part 50 can be formed on the first insulating film 31 and covered with the second insulating film 32 and the third insulating film 33.

In addition, connection pads 60 shown in FIG. 1 can be physically connected to both ends of the heater part 50. The connection pad 60 is in physical contact with the heater part 50 for electrical connection with the heater part 50. The connection pad 60 can also be electrically connected to an electric circuit part outside the insulating part 30.

The heater part 50 heats and activates the catalyst parts 41, 42, 43 and at the same time, the temperature thereof is increased by the reaction heat generated by the reaction between oxygen and hydrogen. The resistance value of the heater part 50 is changed as its temperature changes, and the concentration of hydrogen in the detection space is calculated based on the resistance value of the heater part 50. The connection pad 60 can deliver resistance value information of the heater part 50 to the electric circuit part.

The heater part 50 can be a heating means configured to generate heat by the electric resistance. The heater part 50 can be formed in a predetermined pattern that extends without interruption. At this time, the central portion and both ends of the heater part 50 can be disposed in the insulating part 30. The central portion of the heater part 50 can be formed to pass between the holes 34 of the insulating part 30 in a zigzag shape. For example, the heater part 50 can be made of a molybdenum (Mo) material.

The connection pad 60 can be disposed in a pad hole 35 formed to be recessed in the insulating part 30. The connection pad 60 can be connected to the end of the heater part 50 exposed through the pad hole 35. The connection pad 60 can be connected to the end of the heater part 50 in a state of being in physical contact therewith. The connection pad 60 can be made of a metal material, for example, made of a gold (Au) material.

At this time, the insulating part 30 can have the pad hole 35 formed only in a portion where the connection pad 60 is in contact with the heater part 50. In other words, the insulating part 30 exposes the heater part 50 only through the pad hole 35.

The pad hole 35 is formed to penetrate the second insulating film 32 and the third insulating film 33. The pad hole 35 can be formed to extend from the lower end of the second insulating film 32 to the upper end of the third insulating film 33. The pad hole 35 can be disposed to be stacked on the upper surface of the heater part 50.

The hydrogen sensor according to the exemplary embodiment of the present disclosure configured as described above has the plurality of holes 34 formed in the insulating part 30 to increase the total surface area of the catalyst deposited on the surface of the insulating part 30, thereby improving hydrogen sensing performance. According to the present disclosure, it is possible to maximize the total surface area of the catalyst parts 41, 42, 43 by optimizing the size, etc. of the hole 34.

As the second catalyst part 42 is coated on the surface of the hole 34, the surface area of the catalyst increases, and at the same time, as the hole 34 is formed in the insulating part 30, the surface area of the catalyst formed on the upper end of the insulating part 30 is decreased. Therefore, it is possible to maximize the total surface area of the catalyst deposited on the insulating part 30 (i.e., the first to third catalyst parts 41, 42, 43) by optimizing the size of the hole 34. The total surface area of the catalyst parts 41, 42, 43 can be changed depending on the size of the hole 34, the thickness of the insulating part 30, etc. For example, a diameter of the hole 34 can be 2 μm.

As the diameter of the hole 34 decreases, the amount of surface area reduction of the first and third catalyst parts 41, 43 is decreased, and therefore, the diameter of the hole 34 can be set as a minimum value within a possible range. In addition, as a length in a height direction of the hole 34 increases, the surface area of the second catalyst part 42 increases but there are limitations in process and cost, and therefore, the length of the hole 34 is set as an appropriate value. At this time, the length of the hole 34 can be determined as a value obtained by summing the thickness of the insulating part 30, the thickness of the first catalyst part 41, and the thickness of the third catalyst part 43.

For example, the length of the hole 34 can be 1.7 μm. At this time, the thickness of the first insulating film 31 can be 0.5 μm, the thickness of the second insulating film 32 can be 0.3 μm, the thickness of the third insulating film 33 can be 0.7 μm, and the total thickness of the first catalyst part 41 and the third catalyst part 43 can be 0.2 μm. A loss area of the first and third catalyst parts 41, 43 lost as the hole 34 with the size (1.7 μm) is formed in the insulating part 30 is 5.1 μm2, and an area increased as the second catalyst part 42 is formed on the surface of the hole 34 is about 2.1 times the loss area.

Figure 3:
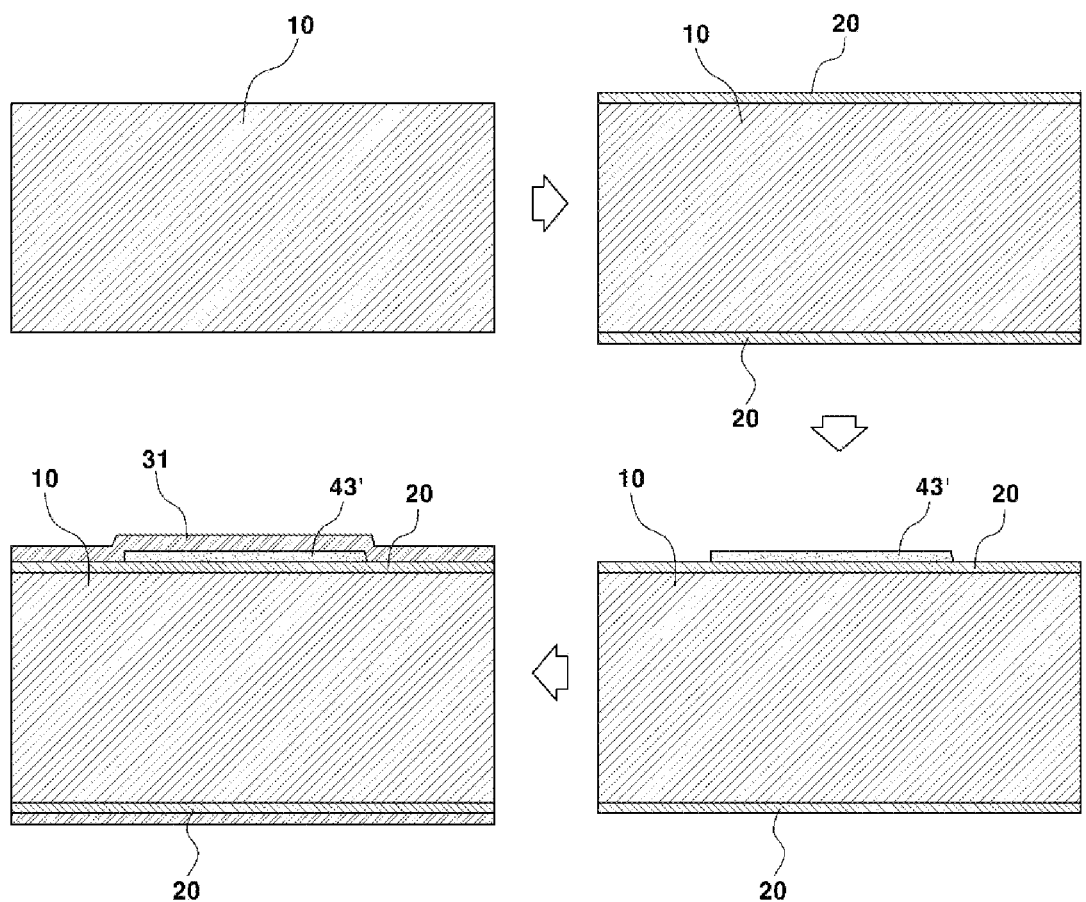
FIGS. 3, 4, and 5 are diagrams showing a manufacturing process of the hydrogen sensor according to the exemplary embodiment of the present disclosure.
Figure 4:
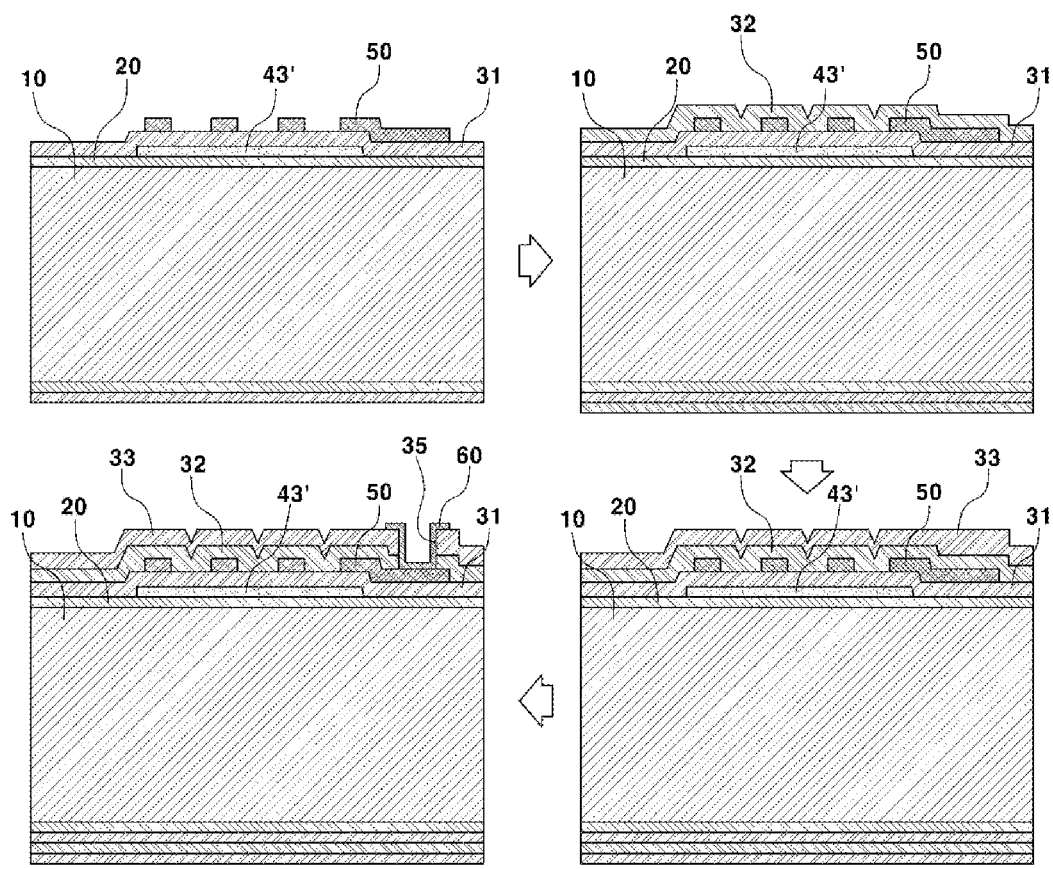
Figure 5:
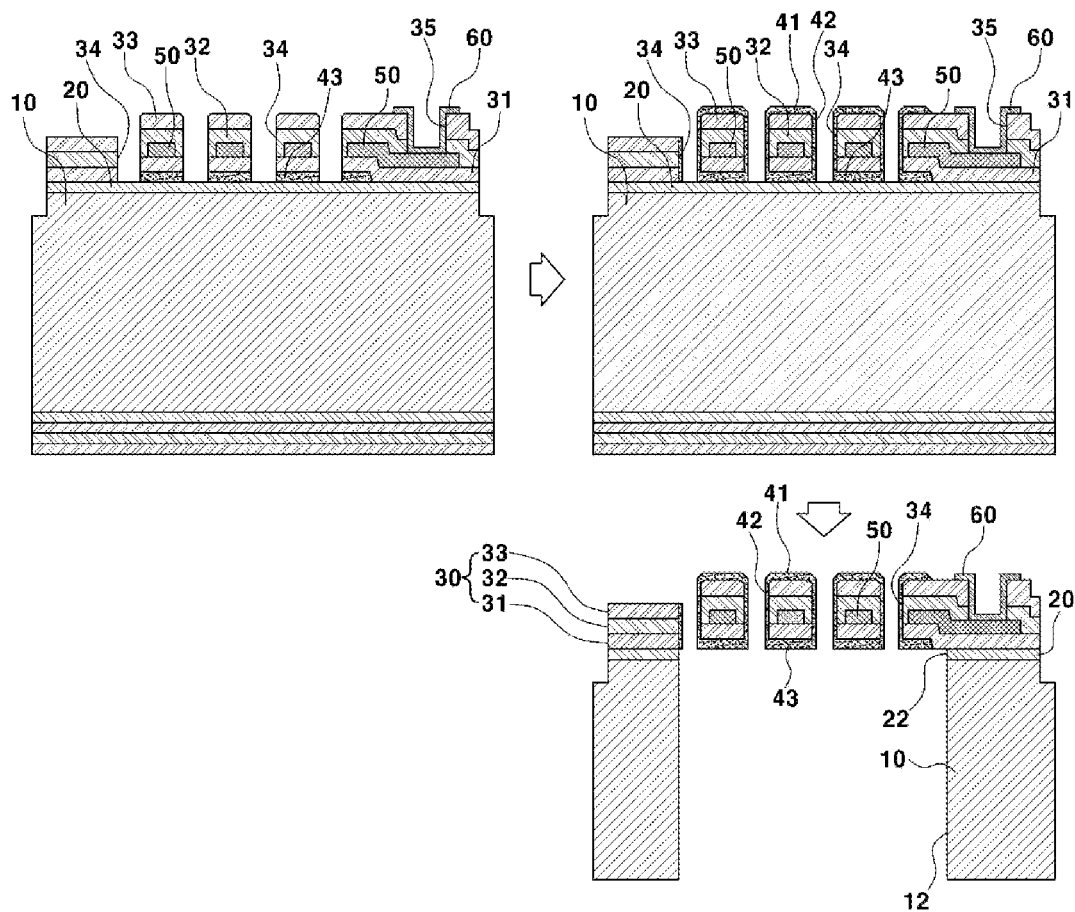

The hydrogen sensor according to the present disclosure configured as described above can be manufactured through the manufacturing process shown in FIGS. 3 to 5. FIGS. 3 to 5 are diagrams sequentially showing a process of manufacturing the hydrogen sensor according to the exemplary embodiment of the present disclosure.

First, as shown in FIG. 3, the substrate 10 is prepared by being manufactured in a plate shape having a predetermined thickness, and the thin film part 20 is formed on the surface of the substrate 10. The thin film part 20 can be formed by depositing silicon oxide on the surface of the substrate 10.

Then, a lower catalyst part 43' is formed on one side surface of the thin film part 20. In other words, the lower catalyst part 43' is formed on the upper end of the thin film part 20. The lower catalyst part 43' becomes the third catalyst part 43 shown in FIG. 1. The lower catalyst part 43' can be formed by depositing platinum on the surface of the thin film part 20 in a predetermined pattern.

Then, the first insulating film 31 is formed on the thin film part 20 on which the lower catalyst portion 43' is formed. In other words, the first insulating film 31 is formed on the surfaces of the lower catalyst part 43' and the thin film part 20. At this time, the first insulating film 31 is coated on the surface of the thin film part 20 to cover the lower catalyst part 43'. The first insulating film 31 can be formed by depositing silicon nitride on the surface of the thin film part 20 and the surface of the lower catalyst part 43'. In addition, the first insulating film 31 can be formed to be stepped on an edge portion of the lower catalyst part 43' because it is formed to be deposited on the lower catalyst part 43'.

Subsequently, as shown in FIG. 4, the heater part 50 is formed on the upper end of the first insulating film 31 in a predetermined pattern. The heater part 50 can be formed by depositing molybdenum on the upper end of the first insulating film 31 in a predetermined pattern.

Then, the second insulating film 32 is formed on the surface of the first insulating film 31. In other words, the second insulating film 32 is formed on the first insulating film 31 on which the heater part 50 is formed. In other words, the second insulating film 32 is formed on the surfaces of the heater part 50 and the first insulating film 31. At this time, the second insulating film 32 is coated on the surface of the first insulating film 31 to directly cover the heater part 50. The second insulating film 32 can be formed by depositing silicon oxide on the surfaces of the heater part 50 and the first insulating film 31. After the second insulating film 32 is formed, an annealing process is performed.

Then, the third insulating film 33 is formed on the surface of the second insulating film 32. The third insulating film 33 can be formed by depositing silicon nitride on the surface of the second insulating film 32. The second insulating film 32 and the third insulating film 33 are formed by being deposited on the heater part 50 and therefore, can be formed in a stepped structure around the heater part 50.

Subsequently, one sides of the second insulating film 32 and the third insulating film 33 are etched to form the pad hole 35, and then the connection pad 60 is formed in the pad hole 35. The pad hole 35 is formed to extend from the upper end of the third insulating film 33 to the lower end of the second insulating film 32, and therefore, the upper surface of the heater part 50 can be partially exposed through the pad hole 35.

The connection pad 60 is formed to airtightly cover the pad hole 35. The connection pad 60 can be formed by depositing gold (Au) in the pad hole 35. At this time, gold (Au) is deposited on the surface of the pad hole 35, that is, on the etched portion of the second insulating film 32 and the third insulating film 33. In addition, at this time, the end of the connection pad 60 can extend to the upper end of the insulating part 30. Therefore, the end of the connection pad 60 can be disposed to be stacked on the upper end of the insulating part 30.

Subsequently, as shown in FIG. 5, the plurality of holes 34 penetrating the first insulating film 31, the second insulating film 32, and the third insulating film 33 are formed.

The hole 34 is formed to penetrate the insulating films 31, 32, 33 and at the same time, to also penetrate the lower catalyst part 43' formed on the upper end of the thin film part 20. In other words, the hole 34 is formed to extend from the upper end of the third insulating film 33 to the lower end of the lower catalyst part 43'. The cross section of the hole 34 is not limited to the circular shape, and can be formed to have cross sections of various shapes such as a hexagon or a square.

Next, the first catalyst part 41 and the second catalyst part 42 are formed on the upper end of the third insulating layer 33 and on the surface of the hole 34. The first catalyst part 41 can be formed by depositing platinum used as a catalyst on the upper end of the third insulating layer 33 in a predetermined pattern, and the second catalyst part 42 can be formed by depositing platinum entirely on the surface of the hole 34.

Then, the through parts 12, 22 are formed in the central portions of the substrate 10 and the thin film part 20 by partially etching the substrate 10 and the thin film part 20. The through parts 12, 22 can be formed to extend from the upper end of the thin film part 20 to the lower end of the substrate 10. In addition, the through parts 12, 22 are formed to communicate with the hole 34 extending to the lower end of the lower catalyst part (i.e., the third catalyst part). After the through parts 12, 22 are formed, the substrate 10 is polished.

Meanwhile, the hydrogen sensor according to the exemplary embodiment of the present disclosure can also be manufactured in the manufacturing process as shown in FIG. 6. FIG. 6 is a diagram showing a manufacturing process of a hydrogen sensor according to another exemplary embodiment of the present disclosure.

As shown in FIG. 6, first, the thin film part 20, the first insulating film 31, the heater part 50, the second insulating film 32, the third insulating film 33, and the first catalyst part 41 are sequentially deposited and formed on the substrate 10, and then, the hole 34 penetrating the first catalyst part 41 and the insulating films 31, 32, 33 is formed, and the substrate 10 and the thin film part 20 are etched to form the through parts 12, 22 in the central portion thereof.

Next, the catalyst (i.e., platinum) is deposited on the surface of the hole 34 and the lower end of the first insulating film 31 in a state of covering the lower end of the substrate 10 with a shadow mask to form the second catalyst part 42 and the third catalyst part 43.

As the exemplary embodiments of the present disclosure have been specifically described above, the terms or words used in the present specification and claims should not be construed as being limited to conventional or dictionary meanings, and in addition, the scope of the present disclosure is not limited to the aforementioned exemplary embodiments, and various modifications and improvements by those skilled in the art using the basic concept of the present disclosure defined in the appended claims also fall within the scope of the present disclosure.

The invention claimed is:

1. A hydrogen sensor comprising:
a substrate;
an insulating part formed on the substrate and comprising a plurality of holes;
a first catalyst part formed on an upper end of the insulating part, and configured to accelerate a reaction between hydrogen and oxygen;
a second catalyst part formed on a surface each of the plurality of holes, and configured to accelerate the reaction between hydrogen and oxygen; and
a heater part disposed inside the insulating part, and configured to heat the first catalyst part and the second catalyst part, and having a temperature increased by reaction heat generated by the reaction between hydrogen and oxygen.

2. The hydrogen sensor of claim 1, wherein a thin film part protecting the insulating part is formed on the upper end of the substrate, and the thin film part is positioned under the insulation part.

3. The hydrogen sensor of claim 2, wherein a third catalyst part is formed on a lower end of the insulating part, the substrate and the thin film part each having a through part formed in a central portion, and the third catalyst part being positioned above the through part.

4. The hydrogen sensor of claim 3, wherein each of the plurality of holes extends from the upper end to the lower end of the insulating part to communicate with the through part.

5. The hydrogen sensor of claim 1, wherein the second catalyst part has a thickness smaller than a radius of each of the plurality of holes.

6. The hydrogen sensor of claim 3, wherein the insulating part comprises:
a first insulating film stacked on an upper end of the thin film part, and having the third catalyst part positioned on a lower end of the first insulating film;
a second insulating film formed on an upper end of the first insulating film to cover the heater part; and
a third insulating film formed on an upper end of the second insulating film.

7. The hydrogen sensor of claim 6, further comprising a connection pad penetrating the second insulating film and the third insulating film to be in contact with a surface of the heater part.

8. A method for manufacturing a hydrogen sensor, the method comprising:
manufacturing and preparing a substrate, and forming a thin film part on the substrate;
forming a lower catalyst part by depositing a catalyst accelerating a reaction between hydrogen and oxygen on the thin film part;
forming a first insulating film on the thin film part to cover the lower catalyst part;
forming a heater part on an upper end of the first insulating film in a predetermined pattern;
forming a second insulating film on the first insulating film to cover the heater part;
forming a third insulating film on an upper end of the second insulating film;
forming a plurality of holes penetrating the insulating films and the lower catalyst part;
forming a first catalyst part and a second catalyst part by depositing a catalyst on an upper end of the third insulating film and a surface of the hole; and
forming a through part in central portions of the substrate and the thin film part by etching the substrate and the thin film part.

9. The method of claim 8, further comprising forming a pad hole by etching the second insulating film and the third insulating film and then, forming a connection pad in contact with the surface of the heater part in the pad hole.

10. The method of claim 9, wherein the forming of the connection pad is performed between the forming of the third insulating film and the forming of the first catalyst part and the second catalyst part.

* * * * *